(12) United States Patent
Zhao et al.

(10) Patent No.: US 7,868,131 B2
(45) Date of Patent: *Jan. 11, 2011

(54) METHODS OF PREPARING POLYMERS HAVING TERMINAL AMINE GROUPS

(75) Inventors: Hong Zhao, Edison, NJ (US); Belen Rubio, Somerset, NJ (US); Jing Xia, Warren, NJ (US)

(73) Assignee: Enzon Pharmaceuticals, Inc., Bridgewater, NJ (US)

( * ) Notice: Subject to any disclaimer, the term of this patent is extended or adjusted under 35 U.S.C. 154(b) by 932 days.

This patent is subject to a terminal disclaimer.

(21) Appl. No.: 11/508,507

(22) Filed: Aug. 23, 2006

(65) Prior Publication Data

US 2008/0249260 A1 Oct. 9, 2008

Related U.S. Application Data

(63) Continuation-in-part of application No. 11/291,546, filed on Dec. 1, 2005, now abandoned, which is a continuation-in-part of application No. 11/212,901, filed on Aug. 26, 2005, now Pat. No. 7,301,003.

(51) Int. Cl.
*C08G 79/02* (2006.01)
*C08G 79/08* (2006.01)
*C08G 73/00* (2006.01)

(52) U.S. Cl. ............... 528/398; 528/4; 528/394; 528/422; 528/425; 528/480; 528/487; 528/488; 528/492; 528/495

(58) Field of Classification Search ............ 528/398, 528/4, 394, 422, 425, 480, 487, 488, 492, 528/495
See application file for complete search history.

(56) References Cited

U.S. PATENT DOCUMENTS

| | | | |
|---|---|---|---|
| 4,179,337 A | 12/1979 | Davis et al. | |
| 4,179,339 A | 12/1979 | Davis et al. | |
| 5,206,344 A | 4/1993 | Katre et al. | |
| 6,448,369 B1 | 9/2002 | Bentley et al. | |
| 6,828,401 B2 | 12/2004 | Nho et al. | |
| 7,301,003 B2 * | 11/2007 | Zhao et al. | 528/398 |
| 2003/0149307 A1 | 8/2003 | Hai et al. | |

FOREIGN PATENT DOCUMENTS

GB 2337523 11/1999

OTHER PUBLICATIONS

Supplementary European Search Report issued in European Patent Application No. 06802202.9 and dated Jun. 24, 2009.
Frisch, B., et al., "Synthesis of Short Polyoxyethylene-Based . . . ", Bioconjugate Chem., vol. 7, p. 180-186, 1996.
Zalipsky, S., et al., Eur. Polym. J. 19:1177-1183, 1983.
Mutter, M., Tetrahedron Lett., 2839-2842, 1978.
Renil, M., et al., J. Peptide Sci., 195-210, 1998.
Mongondry, P., Macromol. Rapid Commun., 24:681-685, 1998.
Yinglin, H., Synth. Commun., 21:79-84, 1991.
Pal, B., Synth. Commun., 34:1317-1323, 2004.
Ragnarsson, U., Acc. Chem. Res., 24:285-289, 1991.
International Search Report and Written Opinion issued in PCT/US06/32971 and dated Mar. 21, 2007.
European Search Report issued in European Patent Application No. 06 802 202.9 and dated May 3, 3010.

* cited by examiner

*Primary Examiner*—Duc Truong
(74) *Attorney, Agent, or Firm*—Lucas & Mercanti, LLP

(57) ABSTRACT

The present invention is directed to methods of preparing linear polymers such as polyalkylene oxides containing a terminal amine in high purity. One preferred method includes reacting a polyalkylene oxide such as polyethylene glycol containing a terminal azide with a phosphine-based reducing agent such as triphenylphosphine or an alkali metal borohydride reducing agent such as sodium borohydride in a solvent to reflux. The resultant polymer-amines are of sufficient purity so that expensive and time consuming purification steps required for pharmaceutical grade polymers are avoided.

24 Claims, No Drawings

METHODS OF PREPARING POLYMERS HAVING TERMINAL AMINE GROUPS

CROSS-REFERENCE TO RELATED APPLICATIONS

This application is a continuation-in-part of U.S. patent application Ser. No. 11/291,546, filed Dec. 1, 2005 now abandoned, which is a continuation-in-part of U.S. patent application Ser. No. 11/212,901, filed Aug. 26, 2005 now U.S. Pat. No. 7,301,003, the contents of each of which are incorporated herein by reference in its entirety.

FIELD OF THE INVENTION

The present invention relates to methods of preparing activated polymers such as polyalkylene oxides. In particular, the invention relates to methods of preparing linear polymers containing a terminal amine in high purity.

BACKGROUND OF THE INVENTION

The conjugation of water-soluble polyalkylene oxides with therapeutic moieties such as proteins and polypeptides is known. See, for example, U.S. Pat. No. 4,179,337, the disclosure of which is hereby incorporated by reference. The '337 patent discloses that physiologically active polypeptides modified with PEG circulate for extended periods in vivo, and have reduced immunogenicity and antigenicity.

To conjugate polyalkylene oxides, the hydroxyl endgroups of the polymer must first be converted into reactive functional groups. This process is frequently referred to as "activation" and the product is called an "activated polyalkylene oxide." Other polymers are similarly activated.

Amine terminated polymers such as PEG-NH$_2$ are known. See Zalipsky et al. Eur. Polym. J. (1983) Vol. 19 No. 12., pp 1177-1183. They can be used "as is" for direct conjugation to COOH groups found on some biologically active compounds. More often, PEG-NH$_2$ (or PEG-amine) is used as an intermediate which is further functionalized when other polymeric delivery systems are desired. For example, certain polymer-based drug delivery platform systems containing benzyl elimination systems, trimethyl lock systems, etc. can include PEG-NH$_2$ as a key intermediate in the process of synthesis. See Greenwald et al. J. Med. Chem. Vol. 42, Sep. 9, 1999; No. 18, 3657-3667; Greenwald et al. J. Med. Chem. Jan. 29, 2004; Vol. 47, No. 3, 726-734; Greenwald et al. J. Med. Chem. Feb. 10, 2000; Vol. 43, No. 3, 475-487. The contents of each of the foregoing are hereby incorporated herein by reference.

PEG-amines are also useful for conjugation (via reductive amination) with biologically active small molecules and polypeptides having available aldehyde groups. See also Nektar Advanced PEGylation catalog 2005-2006, page 24, the contents of which are incorporated herein by reference.

In the past, it was generally known that PEG-amines could be prepared by preparing the PEG-halide, mesylate or tosylate from PEG-OH and thereafter performing a nucleophilic displacement reaction with aqueous ammonia (Hoffmann Reaction), sodium azide or potassium phthalimide (Gabriel Reagent). The reaction of the PEG-halide with the ammonia forms the PEG-amine directly. More importantly, a major disadvantage is that a significant percentage of PEG-halide becomes hydrolyzed to form PEG-OH during the concentrated aqueous ammonia treatment. This is a particular concern when forming higher molecular weight PEG-amines. The higher molecular weight PEG, the more PEG-OH is formed. For example, in the case of PEG$_{5,000}$ the amount is about 5% and with higher molecular weight PEG such as PEG$_{40,000}$ the amount can be up to 20%. Consequently, the purity of the desired end product can decrease considerably.

Even when PEG-azide is used as the intermediate to make the PEG-amine, certain shortcomings have been observed when metal catalyzed hydrogenation is used. Furthermore, reaction with potassium phthalimide provides a basically protected amine that is deprotected with hydrazine in ethanol under reflux. This too is associated with drawbacks. The harsh conditions required for removal of the phthaloyl group and the need for intensive purification of the final product add significantly to the cost of the desired product.

In view of the foregoing, it would be desirable to provide improved methods for preparing PEG-amines and related polymers having terminal amines which address the shortcomings and drawbacks of the prior art. The present invention addresses this need.

SUMMARY OF THE INVENTION

In one preferred aspect of the invention, there are provided improved methods of preparing polymers having terminal amines. The methods include reacting a substantially non-antigenic polymer of the formula (I)

$$R_1-R_2-N_3 \qquad (I)$$

wherein

R$_1$ is a capping group or N$_3$; and

R$_2$ is a substantially non-antigenic polymer;

with a phosphine-based reducing agent or an alkali metal borohydride reducing agent.

The reaction of the polymer-azide with the phosphine-based reducing agent is preferably carried out in a polar solvent and the reactants are reacted under reflux conditions for a time which is sufficient to substantially complete the reaction and cause formation of the terminal amine on the polymer. In more preferred aspects of the invention, the polymer which is converted to the amine derivative is a PEG-azide and the azide group can be on at least one or more of the terminals of the PEG. One preferred phosphine-based reducing agent is triphenylphosphine. In an alternative aspect of the invention, the preferred alkali metal borohydride is NaBH$_4$.

The purity of the polymer containing the terminal amine formed by process described herein is greater than about 95%, preferably greater than 98% and more preferably greater than 99%.

One of the chief advantages of the present invention is that the resulting terminal amine-containing polymers such as polyalkylene oxide derivatives thereof are prepared in high purity. Thus, product contaminants, namely, the starting materials, such as mPEG-OH are not found in appreciable amounts, that is, they are found in amounts of less than about 5%, preferably less than about 2% and most preferably less than about 1%. When the preferred PEG-amines are more economically formed in high purity, the artisan can make the end product which incorporates the PEG-amine more efficiently and at lower cost. The reaction to make the PEG-amine can be forced to completion and the excess small molecule reagents can be removed by recrystallization. The efficiencies result, in part, because the separation of the desired amine-terminated polymer from the starting alcohol or reactive intermediate (e.g. tosylate) is not required. Furthermore, column chromatography based purification techniques are not required to provide the desired PEG-amine. Thus, the present invention provides highly pure PEG-amine without costly column purification.

Another advantage is the fact that the amine made from the processes described herein will not change the backbone of the PEG at all. Therefore, it will be compatible with all current and future applications for PEG amines.

DETAILED DESCRIPTION OF THE INVENTION

The methods of the invention relate generally to the formation of polymers containing at least one terminal amine thereon. In most aspects of the invention, the polymers which can be modified using the processes described herein are substantially non-antigenic polymers. Within this genus of polymers, polyalkylene oxides are preferred and polyethylene glycols (PEG) are most preferred. For purposes of ease of description rather than limitation, the process is sometimes described using PEG as the prototypical polymer. It should be understood, however, that the process is applicable to a wide variety of polymers which can be linear, substantially linear, branched, etc. One of the only requirements is that the polymer contains the means for covalently attaching an azide thereon and can withstand the processing required to transform the azide to the amine under the conditions described herein.

In accordance with the foregoing, one preferred aspect of the invention for preparing a polymer having a terminal amine, includes:

reacting a substantially non-antigenic polymer of the formula (I)

$$R_1—R_2—N_3 \quad (I)$$

wherein
$R_1$ is a capping group or $N_3$; and
$R_2$ is a substantially non-antigenic polymer;
with a phosphine-based reducing agent or an alkali metal borohydride reducing agent.

As stated above, $R_1$ is a capping group. For purposes of the present invention, capping groups shall be understood to mean a group which is found on the terminal of the polymer. In some aspects, it can be selected from any of $CO_2H$, $C_{1-6}$ alkyls ($CH_3$ preferred), OH, etc. or other terminal groups as they are understood by those of ordinary skill.

$R_2$ is also preferably a polymer that is water soluble at room temperature such as a polyalkylene oxide (PAO) and more preferably a polyethylene glycol such as mPEG or bis-activated PEG. A non-limiting list of such polymers therefore includes polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

For purposes of illustration and not limitation, the polyethylene glycol (PEG) residue portion of $R_2$ can be
$—CH_2CH_2—O—(CH_2CH_2O)_x—CH_2CH_2—$
wherein:
x is the degree of polymerization, i.e. from about 10 to about 2,300. Thus, in one aspect of the invention where the capping group of $R_1$ is $CH_3$ and $R_2$ is PEG, the mono-activated polymer can be of formula (Ib):

$$CH_3—O—(CH_2CH_2O)_x—CH_2CH_2—N_3. \quad (Ib)$$

In alternative aspects of the invention, when bis-activated polymers are desired, $R_1$ is $N_3$, and the resultant reactant is used in making the bis-amine-terminated polymer compounds. Such bis-activated polymers can be of formula (Ia):

$$N_3—CH_2CH_2—O—(CH_2CH_2O)_x—CH_2CH_2—N_3 \quad (Ib)$$

wherein x is the same as above.

The degree of polymerization for the polymer represents the number of repeating units in the polymer chain and is dependent on the molecular weight of the polymer. Although substantially non-antigenic polymers, PAO's and PEG's can vary substantially in weight average molecular weight, preferably, $R_2$ has a weight average molecular weight of from about 200 to about 100,000 Daltons in most aspects of the invention. More preferably, the substantially non-antigenic polymer has a weight average molecular weight from about 2,000 to about 48,000 Daltons.

$R_2$ can also be a "star-PEG" or multi-armed PEG's such as those described in NOF Corp. Drug Delivery System catalog, Ver. 8, April 2006, the disclosure of which is incorporated herein by reference.

In yet another preferred embodiment, $R_2$ is part of a branched polymer corresponding to the polymers of the invention. Specifically, $R_2$ can be of the formula:

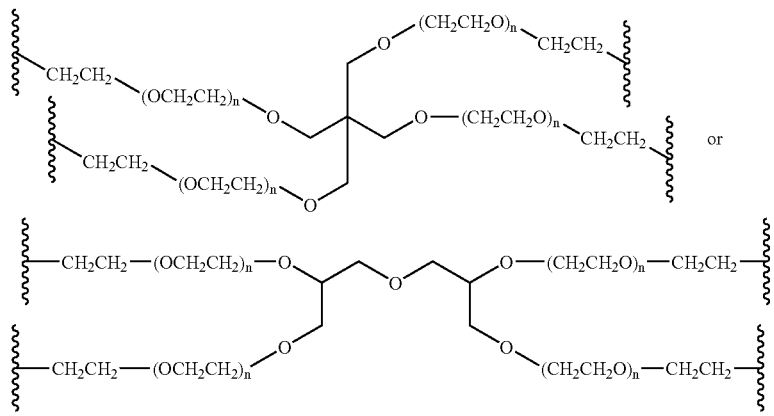

wherein:

n is an integer from about 10 to about 340, to preferably provide polymers having a total molecular weight of from about 12,000 to about 40,000; and at least 1, but up to 3, of the terminal portion a of the residue is/are capped with a methyl or other lower alkyl See also the aforementioned Nektar catalog, page 26 "4-arm PEG." Such compounds prior to terminal amination preferably include:

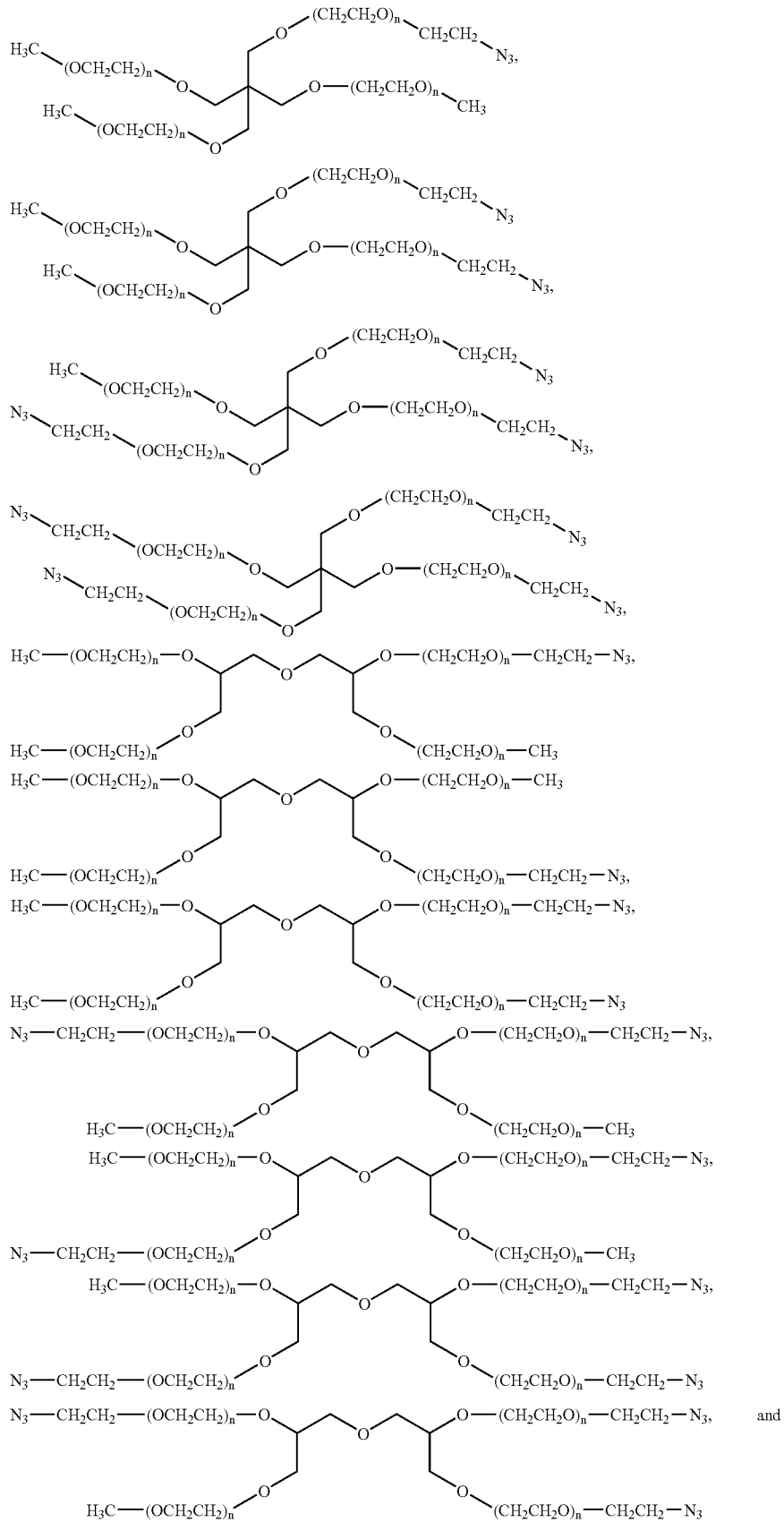

-continued

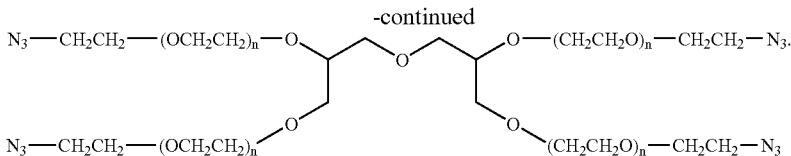

Also contemplated within the scope of the invention, is the formation of a terminal amine on various other PEG-based compounds, including those branched polymer residues described in commonly assigned U.S. Pat. Nos. 5,605,976, 5,643,575, 5,919,455 and 6,113,906, the disclosure of each being incorporated herein by reference. A representative list of some specific compounds includes:

(2a)
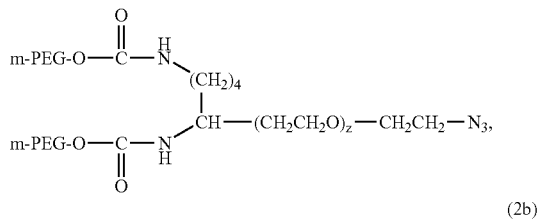

(2b)
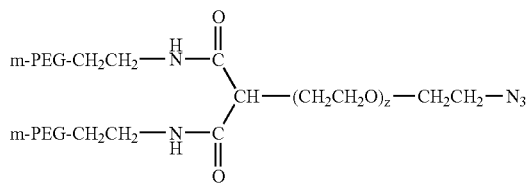
and (2c)
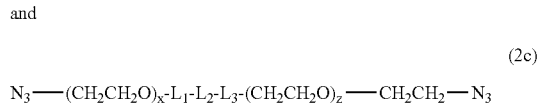

wherein z is an integer from 1 to about 120;

$L_1$ and $L_3$ are independently selected bifunctional linking groups such as one of the following non-limiting compounds:

—NH(CH$_2$CH$_2$O)$_y$(CH$_2$)$_q$NR$_9$—,

—NH(CH$_2$CH$_2$O)$_y$C(O)—, —NH(CR$_{10}$R$_{11}$)$_q$OC(O)—,

—C(O)(CR$_{10}$R$_{11}$)$_q$NHC(O)(CR$_{13}$R$_{12}$)$_q$NR$_9$—,

—C(O)O(CH$_2$)$_q$O—, —C(O)(CR$_{10}$R$_{11}$)$_q$NR$_9$—

—C(O)NH(CH$_2$CH$_2$O)$_y$(CH$_2$)$_q$NR$_9$—,

—C(O)O⁻(CH$_2$CH$_2$O)$_y$NR$_9$—,

—C(O)NH(CR$_{10}$R$_{11}$)$_q$O—, —C(O)O(CR$_{10}$R$_{11}$)$_q$O—,

—C(O)NH(CH$_2$CH$_2$O)$_y$—,

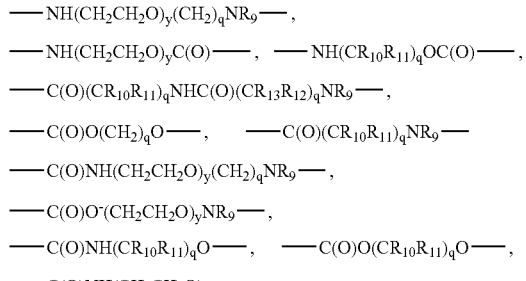
and

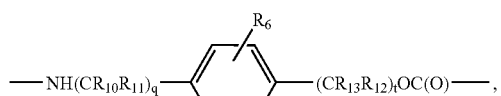

-continued
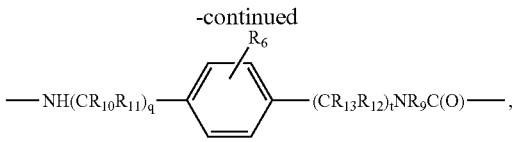

wherein $R_{9-13}$ are independently selected from the same group as $C_{1-6}$ alkyls, etc. and preferably H or CH$_3$;

$R_6$ is selected from the same group as that which defines $R_{9-13}$, NO$_2$, $C_{1-6}$ halo-alkyl and halogen; and q, t and y are each independently selected positive integers such as from 1 to about 12; and $L_2$ is a branched linking group such as a diamino alkyl or lysine residue. See, for example, the aforementioned U.S. Pat. No. 6,113,906, for example.

In a further embodiment, and as an alternative to PAO-based polymers, $R_2$ is optionally selected from among one or more effectively non-antigenic materials such as dextran, polyvinyl alcohols, carbohydrate-based polymers, hydroxypropylmethacryl-amide (HPMA), polyalkylene oxides, and/or copolymers thereof. See also commonly-assigned U.S. Pat. No. 6,153,655, the contents of which are incorporated herein by reference. It will be understood by those of ordinary skill that the same type of activation is employed as described herein as for PAO's such as PEG. Those of ordinary skill in the art will further realize that the foregoing list is merely illustrative and that all polymeric materials having the qualities described herein are contemplated.

It will also be understood that the water-soluble polymer can be functionalized for attachment to the azide group(s) if required without undue experimentation prior to amination.

One of the reactants required for the process of preparing the desired amine-terminated polymer is the azide (N$_3$) terminated starting material. The preparation of such azide modified polymers has been reported in the literature, see for example the aforementioned Zalipsky, Eur. Polym. J. (1983). Alternatively, the azide can be made by reacting a compound of formula (II):

$$R_3—CH_2CH_2—O—(CH_2CH_2O)_x—CH_2CH_2—R_3 \qquad (II)$$

wherein $R_3$ is selected from the group consisting of Br, Cl, tosylate or mesylate, brosylate, tresylate, nosylate; and x is the degree of polymerization;

with NaN$_3$ in the presence of a solvent such as ethanol and/or DMF.

In one aspect of the invention, the conversion of the PEG-azide to the corresponding amine can be accomplished when the azide and phosphine-based reducing agent are reacted in a solvent and the reactants are allowed to reflux for a time sufficient to cause formation of the terminal amine on the polymer.

There are a number of suitable phosphine-based reducing agents which can be used in the process of the invention. A non-limiting list includes reducing agents such as triphenylphosphine, tritolylphosphine, tributylphosphine, tert-butyldiphenylphosphine, diphenyl(p-tolyl)phosphine, tris(2,4,6-trimethoxyphenyl)phosphine, tris(2,6-dimethoxyphenyl)phosphine, tris(2-methoxyphenyl)phosphine, tris(3-chlorophenyl)phosphine, tris(3-methoxyphenyl)phosphine, tris(4-fluorophenyl)phosphine, tris(4-methoxyphenyl)-phosphine, tris(p-chlorophenyl)phosphine, and tris(pentafluorophenyl)phosphine. Preferably, the phosphine-based reducing agent is triphenylphosphine.

There are also a number of suitable solvents which can be used in the process of the present invention. Suitable solvents include those which are polar solvent such as consisting of methanol, ethanol, butanol, isopropanol, tetrahydrofuran (THF), dimethylformamide (DMF) and dioxane. Methanol is the preferred solvent.

In an alternative aspect of the invention, an alkali metal borohydride reducing agent is used for the conversion of the PEG-azide to the PEG-amine. Suitable alkali metal borohydride reducing agents reagents include but are not limited to sodium borohydride, (preferred), lithium borohydride and potassium borohydride. Others will be apparent to those of ordinary skill. When this route is selected for amination, the reduction of the azide using the alkali metal borohydride reducing agent is carried out in a $C_{1-6}$ alcohol, with isopropyl alcohol, methanol or ethanol being preferred.

The methods of the present invention are preferably carried out using at least about an equimolar amount of the reactants. More preferably, the phosphine-based reducing agent is present in a molar excess with respect to the compound of formula (I) when the polymer has only one azide. A preferred ratio of triphenylphosphine to mPEG is about 5 to about 1. More preferably, the ratio is about 3 to 1. When delta-PEG (bis-PEG or activated on each terminal) is used, the ratio is about 10 to about 2, preferably 6 to 2. Similar ratios are used per amine group to be added if branched polymers are used. The amount of the phosphine-based reducing agent present in the reaction is preferably about at least about a two-fold to molar excess with respect to the compound of formula (I) when bis-azide polymer is used. It will be understood that when terminally branched polymers are used, the molar excess of phosphine-based reducing agent preferably used is at least equal to the number of azide moieties found on the polymer.

In the case of the alkali metal borohydride, it is preferred that there is at least about a ten-fold molar excess of the borohydride to the polymer. More preferably, there is about a 15-fold molar excess. The molar excess can be as high as 50- or 100-fold, if desired.

The methods of the present invention are preferably carried out under reflux conditions, i.e. at a temperature of about the boiling point or slightly above of the solvent.

The high-purity PEG-amine can then be used in any art-recognized way. For example, and without limitation, it can be used for direct conjugation with $CO_2H$ groups or other suitable reactive groups found on biologically active targets of interest using techniques well known to those of ordinary skill. Alternatively, the PEG-amine can be used as a highly pure intermediate in more complex polymer linking systems such as the aforementioned benzyl-elimination (RNL) platforms or even as part of PEG-liposome systems. For the sake of illustration, the RNL systems can be made by reacting the PEG-amine with a suitable protected benzyl alcohol followed by deprotection and activation using techniques known to those of ordinary skill. See also the last example below.

In many aspects of the invention, a polyalkylene oxide (PAO) such as uncapped PEG-OH (di-PEG OH) or mPEG is converted into a compound of formula (IIa) or (IIb):

$$N_3-R_2-N_3 \quad (IIa)$$

or $$R_1-R_2-N_3 \quad (IIb)$$

wherein:
$R_1$ is methyl; and
$R_2$ is a PAO such as PEG.

After the polymer containing the azide is formed, it is converted as described herein to form the desired PEG-amine derivatives in high purity. The high purity PEG-amine can then be used in any art-recognized way.

EXAMPLES

The following examples serve to provide further appreciation of the invention but are not meant in any way to restrict the effective scope of the invention.

Example 1

PEG-amine

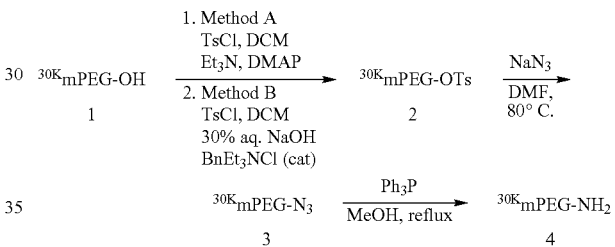

Scheme 1

PEG-tosylate (PEG-OTs).

Method A. A solution of $^{20KDa}\Delta$PEG-OH (i.e. bis-PEG-OH) (2.8 g, 0.14 mmol) was azeotroped for 2 hours in toluene. The toluene was removed under vacuum and the solid residue was redissolved in 50 mL of anhydrous dichloromethane (DCM). To this solution was added triethylamine (195 μL, 1.4 mmol) and 4-dimethylaminopyridine (DMAP) (165 mg, 1.35 mmol). The mixture was cooled in an ice bath and p-toluenesulfonyl chloride (267 mg, 1.4 mmol) in DCM was then added dropwise. The reaction mixture was gradually warmed to room temperature and stirred overnight. The reaction mixture was washed twice with a 0.1 N HCl solution. The organic phase was evaporated under vacuum. The resulting solid was dissolved in the minimum amount of $CH_2Cl_2$ and then, precipitated by addition of ethyl ether. After filtration the resulting solid was recrystallized with 2-isopropanol (IPA). $^{13}C$ NMR (67.8 MHz, $CDCl_3$) δ 143.92, 132.38, 129.1, 127.29, 67.99-70.22, 21.09.

Method B. To a solution of $^{30KDa}$mPEG-OH (25 g, 0.83 mmol, 1 eq) in 200 mL of DCM were added 150 mL of a 30% aqueous NaOH solution and $BnEt_3NCl$ (76 mg, 0.33 mmol, 0.4 eq). Then, to the vigorously stirred mixture a solution of p-toluenesulfonyl chloride (475 mg, 2.5 mmol, 3 eq) in 150 mL of DCM was added dropwise via addition funnel, and the reaction mixture was stirred at room temperature overnight. After addition of 200 mL of DCM and 200 mL of a saturated NaCl solution, the organic phase was separated and washed twice with 200 mL of a saturated NaCl solution. The organic phase was dried over anhydrous $MgSO_4$, filtered and evaporated under vacuum to give a solid that was dissolved in a minimum amount of DCM and precipitated with ethyl ether. Filtration provided 24 g of $^{30KDa}$mPEG-OTs (96% yield). $^{13}$C NMR: 21.56, 58.86, 68.45, 69.07, 69.96-71.71 (PEG), 127.64, 129.53, 132.70, 144.43. GPC: 100%

PEG-azide (PEG-N$_3$). To a solution of $^{30KDa}$mPEG-OTs (2 g, 0.066 mmol, 1 eq) in 20 mL anhydrous DMF was added NaN$_3$ (13 mg, 0.2 mmol, 3 eq). The reaction mixture was heated to 80° C. overnight and then cooled and evaporated under vacuum. The resulting solid was recrystallized with CH$_3$CN/IPA to give 1.7 g of $^{30KDa}$mPEG-N$_3$ (85% yield). $^{13}$C NMR (ppm): 50.49, 58.84, 69.37-71.72 (PEG). GPC: 99.3%.

PEG-amine (PEG-NH$_2$). To a solution of $^{30KDa}$mPEG-N$_3$ (10.64 g, 0.35 mmol, 1 eq) in 120 mL anhydrous MeOH was added triphenylphosphine (279 mg, 1.06 mmol, 3 eq). The reaction mixture was heated to reflux overnight, cooled and evaporated under vacuum. The resulting solid was dissolved in the minimum amount of DCM and then, precipitated by addition of ethyl ether. After filtration the solid was recrystallized with CH$_3$CN/IPA to give 9.94 g of $^{30KDa}$mPEG-NH$_2$ (95% yield). $^{13}$C NMR (ppm): 41.61, 58.83, 69.42-73.23 (PEG). GPC: 98.91%

The corresponding $^{20KDa}$ΔPEG-azide and $^{20KDa}$ΔPEG-amine are made from the $^{20KDa}$ΔPEG-OTs of Method A.

Example 2

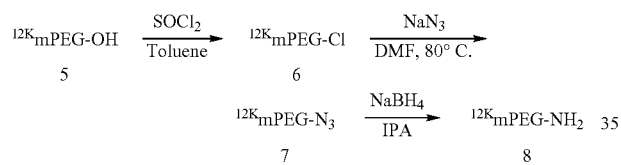

PEG-chloride. A solution of $^{12KDa}$mPEG-OH (12 g, 0.1 mmol) was azeotroped for 2 hours in toluene. This mixture was cooled to 30° C. and thionyl chloride was then added. The reaction mixture was refluxed for 18 hours, followed by partial removal of the solvent, and precipitation of the product with ethyl ether. The solid was collected by filtration, washed with ethyl ether, and recrystallized from isopropanol to yield the product (10.8 g, 0.81 mmol). $^{13}$C NMR (67.8 MHz, CDCl$_3$) δ 69.64-70.9, 42.5.

PEG-azide (PEG-N$_3$). To a solution of $^{12KDa}$mPEG-Cl (10.6 g, 0.883 mmol) in anhydrous DMF was added NaN$_3$ (919 mg, 35.5 mmol). The reaction was heated at 80° C. for 24 hours. After addition of ethyl ether, the solid was collected by filtration. The solid residue was dissolved in DCM and the solution was washed with water three times, dried over NaSO$_4$, filtered and evaporated under vacuum. The resulting solid was recrystallized from DCM/ethyl ether to give the PEG-azide (9.54 g, 0.795 mmol). $^{13}$C NMR (67.8 MHz, CDCl$_3$) δ 69.64-70.9, 50.29.

PEG-amine (PEG-NH$_2$). To a suspension of $^{12KDa}$mPEG-N$_3$ (1.23 g, 0.1 mmol) in IPA was added sodium borohydride (58 mg, 1.5 mmol). The reaction mixture was refluxed overnight. The reaction mixture was cooled to room temperature and ethyl ether was added. The resulting solid was collected by filtration. The solid residue was dissolved in DCM and the solution was washed with water three times, dried over NaSO$_4$, filtered, evaporated under vacuum and recrystallized from IPA to give PEG-amine (1.13 g, 0.09 mmol). $^{13}$C NMR (67.8 MHz, CDCl$_3$) δ 68.42-72.89, 41.53.

Example 3 mPEG$^{30K}$ RNL 9 Linker

In this example, the $^{30KDa}$mPEG-NH$_2$ of Example 1 is converted into the activated PEG linker according to the following reaction scheme.

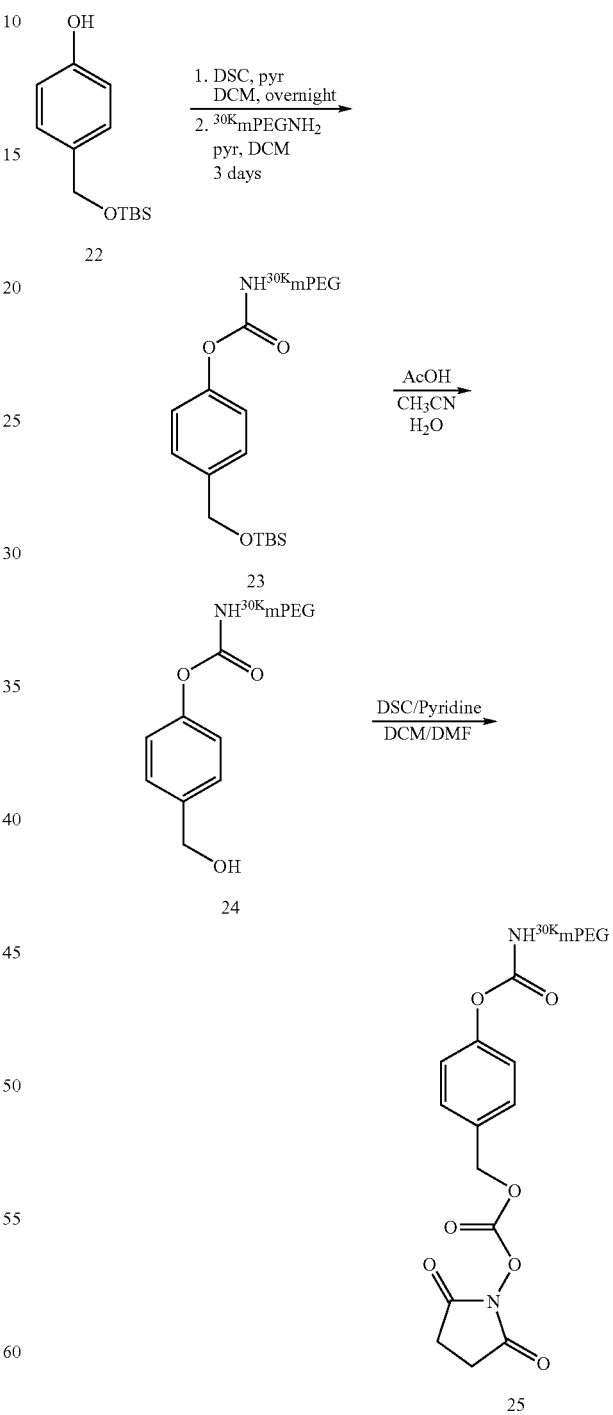

mPEG$^{30K}$ RNL9 OTBDMS 23:

To a solution of alcohol, 22 (238 mg, 1 mmol, 6 eq) in anhydrous CH$_3$Cl were added DSC (235 mg, 0.92 mmol, and 5.5 eq) and pyridine (88 μL, 1.08 mmol, 6.5 eq). The resulting suspension was heated to reflux overnight, cooled to room temperature and added to a solution of $^{30KDa}$mPEG-NH$_2$ (hereinafter 21) (5 g, 0.17 mmol, 1 eq) in 25 mL of anhydrous CH$_3$Cl. After stirring at room temperature for 3 days, the solvent was evaporated under vacuum. The resulting solid was dissolved in the minimum amount of dichloromethane and then, precipitated by addition of ether, filtered and recrystallized with CH$_3$CN/IPA to give 4.85 g (94% yield). GPC: 98.39%. $^{13}$C NMR (75.4 MHz, CDCl$_3$) δ 154.47, 149.59, 137.90, 126.52, 121.02, 69.09-71.65 (PEG), 64.24, 58.83, 40.83, 25.84, 18.27, 5.28.

mPEG$^{30K}$ RNL9OH 24:

To a solution of 23 (4.85 g, 0.16 mmol) in 20 mL CH$_3$CN and 10 mL of water was added 50 mL of glacial acetic acid. The reaction mixture was stirred at room temperature overnight and then, evaporated under vacuum. The residue was dissolved in 75 mL CH$_2$Cl$_2$. The organic phase was washed twice with 15 mL of water, dried over MgSO$_4$, filtered and evaporated under vacuum. The resulting solid was dissolved in the minimum amount of CH$_2$Cl$_2$ and then, precipitated by addition of ether to give 4.49 g (94% yield). GPC: 98.35%. $^{13}$C NMR (75.4 MHz, CDCl$_3$) δ 154.36, 149.90, 138.18, 127.37, 121.15, 69.42-71.69 (PEG), 63.93, 58.80, 40.83.

mPEG$^{30K}$ RNL9NHS 25:

To a solution of 24 (4.49 g, 0.15 mmol, 1 eq) in 50 mL anhydrous CH$_2$Cl$_2$ and 5 mL anhydrous DMF was added DSC (305 mg, 1.19 mmol, 8 eq). The mixture was cooled to 0° C. and then, pyridine (87 μL, 1.07 mmol, 7.2 eq) was added. The reaction mixture was stirred at room temperature overnight and then, evaporated under vacuum. The resulting solid was dissolved in the minimum amount of CH$_2$Cl$_2$ and then, precipitated by addition of ether, filtered and recrystallized with CH$_3$CN/IPA to give 4.26 g (94% yield). GPC: 97.04%. $^{13}$C NMR (75.4 MHz, CDCl$_3$) δ 168.33, 154.01, 151.51, 151.22, 129.80, 129.53, 121.68, 69.88-73.08 (PEG), 58.83, 40.89, 25.32.

The final product can be used for conjugation to any number of biologically active polypeptides, enzymes, proteins, small molecules, etc. having an available amine or hydroxyl thereon for conjugation. The procedures for such conjugation reactions have been described, for example, in commonly-assigned U.S. Pat. No. 6,180,095, the contents of which are incorporated herein by reference, or the aforementioned Greenwald et al. J. Med. Chem. 1999 Vol. 42, No. 18, 3657-3667.

What is claimed is:

1. A method of preparing a polymer having a terminal amine, comprising, reacting a polymer of the formula (I)

R$_1$—R$_2$—N$_3$ (I)

wherein

R$_1$ is a capping group or N$_3$; and

R$_2$ is a substantially non-antigenic polymer;

with a phosphine-based reducing agent or an alkali metal borohydride reducing agent, wherein said reaction is carried out in the presence of a C$_{1-10}$ alcohol, tetrahydrofuran (THF), dimethylformamide, or dioxane.

2. The method of claim 1, wherein R$_2$ is a polyalkylene oxide.

3. The method of claim 1, wherein the R$_1$ capping group is CH$_3$.

4. The method of claim 1, wherein R$_1$ is N$_3$.

5. The method of claim 2, wherein said polyalkylene oxide is selected from the group consisting of polyethylene glycol and polypropylene glycol.

6. The method of claim 5, wherein said polyalkylene oxide is a polyethylene glycol of the formula: —O—(CH$_2$CH$_2$O)$_x$—, wherein x is an integer from about 10 to about 2,300.

7. The method of claim 1, wherein the phosphine-based reducing agent is selected from the group consisting of triphenylphosphine, tri(tolyl)phosphine, tributylphosphine, tert-butyldiphenylphosphine, diphenyl(p-tolyl)phosphine, tris(2,4,6-trimethoxy-phenyl)phosphine, tris(2,6-dimethoxyphenyl)phosphine, tris(2-methoxyphenyl)-phosphine, tris(3-chlorophenyl)phosphine, tris(3-methoxyphenyl)phosphine, tris(4-fluorophenyl)phosphine, tris(4-methoxyphenyl)phosphine, tris(p-chlorophenyl)-phosphine, and tris(pentafluorophenyl)phosphine.

8. The method of claim 7, wherein the phosphine-based reducing agent is triphenylphosphine.

9. The method of claim 1, wherein the alkali metal borohydride reducing agent is selected from the group consisting of sodium borohydride, lithium borohydride and potassium borohydride.

10. The method of claim 9, wherein the alkali metal borohydride reducing agent is sodium borohydride.

11. The method of claim 2, wherein the polyalkylene oxide has a weight average molecular weight from about 200 to about 100,000 Daltons.

12. The method of claim 11, wherein the polyalkylene oxide has a weight average molecular weight from about 2,000 to about 48,000 Daltons.

13. The method of claim 1, wherein said reaction is carried out in a C$_{1-6}$ alcohol.

14. The method of claim 13, wherein the C$_{1-6}$ alcohol is selected from the group consisting of methanol, ethanol, butanol, and isopropanol.

15. The method of claim 14, wherein the C$_{1-6}$ alcohol is methanol; wherein the phosphine-based reducing agent is selected from the group consisting of triphenylphosphine, tri(tolyl)phosphine, tributylphosphine, tert-butyldiphenylphosphine, diphenyl(p-tolyl)phosphine, tris(2,4,6-trimethoxy-phenyl)phosphine, tris(2,6-dimethoxyphenyl) phosphine, tris(2-methoxyphenyl)-phosphine, tris(3-chlorophenyl)phosphine, tris(3-methoxyphenyl)phosphine, tris(4-fluorophenyl)phosphine, tris(4-methoxyphenyl)phosphine, tris(p-chlorophenyl)-phosphine, and tris(pentafluorophenyl)phosphine; and wherein the alkali metal borohydride reducing agent is selected from the group consisting of sodium borohydride, lithium borohydride and potassium borohydride.

16. The method of claim 1, wherein the phosphine-based reducing agent is present in an amount ranging from about equimolar to molar excess with respect to the compound of formula (I).

17. The method of claim 1, wherein the compound of formula (I) is:

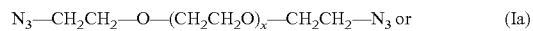
N$_3$—CH$_2$CH$_2$—O—(CH$_2$CH$_2$O)$_x$—CH$_2$CH$_2$—N$_3$ or (Ia)

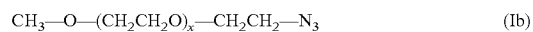
CH$_3$—O—(CH$_2$CH$_2$O)$_x$—CH$_2$CH$_2$—N$_3$ (Ib)

wherein x is the degree of polymerization;

wherein the phosphine-based reducing agent is selected from the group consisting of triphenylphosphine, tri(tolyl)phosphine, tributylphosphine, tert-butyldiphenylphosphine, diphenyl(p-tolyl)phosphine, tris(2,4,6-trimethoxy-phenyl)phosphine, tris(2,6-dimethoxyphenyl)phosphine, tris(2-methoxyphenyl)-phosphine, tris(3-chlorophenyl)phosphine, tris(3-methoxyphenyl)phosphine, tris(4-fluorophenyl)

phosphine, tris(4-methoxyphenyl)phosphine, tris(p-chlorophenyl)-phosphine, and tris(pentafluorophenyl) phosphine; and wherein the alkali metal borohydride reducing agent is selected from the group consisting of sodium borohydride, lithium borohydride and potassium borohydride.

18. The method of claim 16, wherein the phosphine-based reducing agent is present in an amount of at least about a two-fold molar excess with respect to the compound of formula (I).

19. The method of claim 1, wherein the purity of the polymer containing said terminal amine formed by said process is greater than about 95%.

20. The method of claim 19, wherein the purity of the polymer containing said terminal amine formed by said process is greater than 98%.

21. The method of claim 20, wherein the purity of the polymer containing said terminal amine formed by said process is greater than 99%.

22. The method of claim 17, wherein the compound of formula (Ia) is prepared by reacting a compound of formula (II)

$$R_3-CH_2CH_2-O-(CH_2CH_2O)_x-CH_2CH_2-R_3 \quad (II)$$

wherein $R_3$ is selected from the group consisting of Br, Cl, tosylate, mesylate, brosylate, tresylate and nosylate; and x is the degree of polymerization;

with $NaN_3$ in the presence of a solvent.

23. The method of claim 1, wherein the compound of formula (I) is selected from the group consisting of:

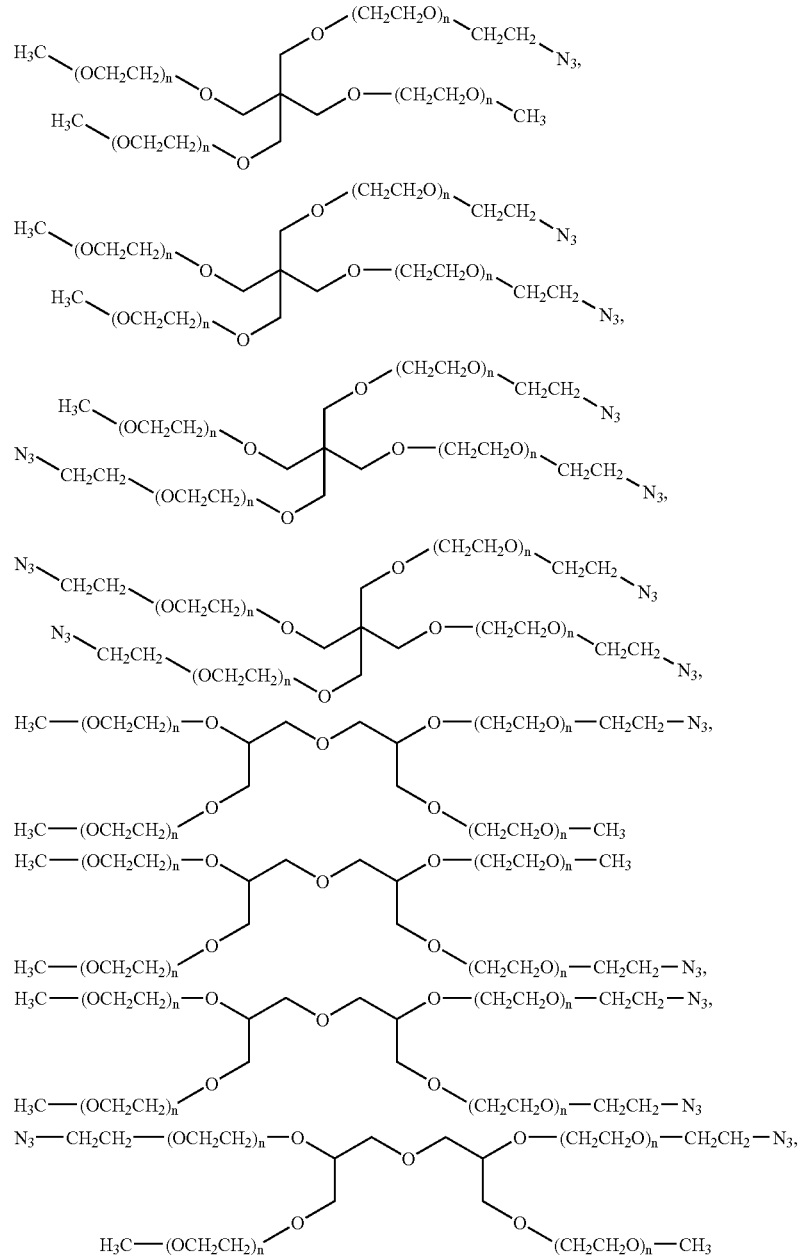

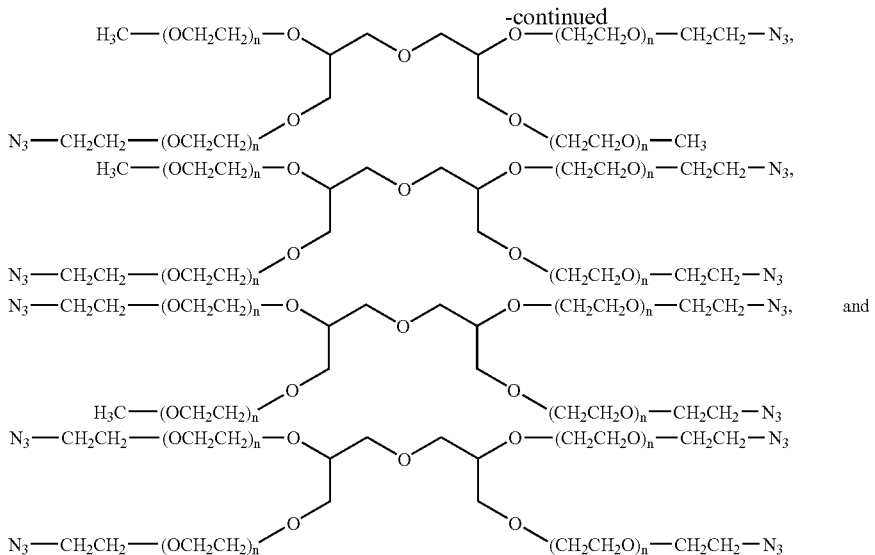
wherein n is an integer from about 10 to about 340.
24. The method of claim 22, wherein $R_3$ is tosylate.
* * * * *